United States Patent [19]

Scandel

[11] Patent Number: 4,832,872

[45] Date of Patent: May 23, 1989

[54] HAIR CONDITIONING SHAMPOO

[75] Inventor: Jean Scandel, Paris, France

[73] Assignee: Richardson-Vicks Inc., Wilton, Conn.

[21] Appl. No.: 147,239

[22] Filed: Jan. 22, 1988

[51] Int. Cl.$^4$ .............................................. C11D 1/62
[52] U.S. Cl. ................. 252/547; 252/174.23; 252/DIG. 2; 252/DIG. 5; 252/DIG. 13; 424/70
[58] Field of Search ............... 252/174.23, DIG. 13, 252/DIG. 5, DIG. 14, DIG. 2, 173, 547; 424/70, 71

[56] References Cited

U.S. PATENT DOCUMENTS

| | | | |
|---|---|---|---|
| 3,904,748 | 9/1975 | Eckert et al. | 424/70 |
| 3,987,162 | 10/1976 | Scheuermann | 252/DIG. 2 |
| 4,009,256 | 2/1977 | Nowak, Jr. et al. | 252/DIG. 13 |
| 4,578,216 | 3/1986 | Fujii et al. | 252/DIG. 13 |
| 4,707,292 | 11/1987 | Sano et al. | 252/DIG. 17 |

OTHER PUBLICATIONS

Lecithin, Hawley's Condensed Chemical Dictionary, 11th Ed., p. 695, Pre. 1988.
Hair Tonics, Cosmetics, Science and Technology, 2nd Ed., pp. 128–130, Pre. 1988.

*Primary Examiner*—Paul Lieberman
*Assistant Examiner*—Hoa Van Le
*Attorney, Agent, or Firm*—David K. Dabbiere; Jack D. Schaeffer; Douglas C. Mohl

[57] ABSTRACT

This invention relates to a new composition for washing and conditioning hair, and more particularly a new composition providing both a shampooing and a conditioning action in a single application.

1 Claim, No Drawings

HAIR CONDITIONING SHAMPOO

Various types of shampoos are known whose composition is generally based on surfactants, which can be anionic, such as an alkyl sulfate, an alkyl ether sulfate an alkyl sulfonate an alkyl sulfosuccinate, or else an alkali metal phosphate, including 12 to 24 carbon atoms in the alkyl moiety or amphoteric, such as N-alkyl amido betaine, or cationic such as an ammonium alkyl acetate, or else non-ionic such as ethoxylated fatty alcohol. These shampoos are normally used in small quantities applied to the hair by the user who, after addition of water and lathering, then rinses it. It is generally necessary to do this twice to obtain a satisfactory result.

These surfactants have a rather irritant action on the scalp in addition, the effect of their detergent action during washing is to remove part of the sebum from the hair, which has a tendency to make it dry and difficult to style. The usual shampoos must therefore include various additives to compensate for the side-effects of surfactants and supplement their action, and it is even necessary, when it is desired to restore and improve the sheen and the flexibility of the hair and its manageability to use a conditioner, applied after shampooing. Moreover, rinsing is essential after applications of the shampoo and the conditioner, that is, it is necessary to proceed in two steps consisting of using the shampoo and then the conditioner, each application being followed by rinsing.

The conditioners habitually used have a relatively acid pH, generally between 3 and 3.5. In addition, it is difficult to combine a shampoo and a conditioner in a single composition, as the properties of such a combination are difficult to anticipate because of the interactions of the various components, and even when there is compatibility between the various components, their properties usually prove to be antagonistic to enable simultaneously washing of the hair and reconditioning of the hair to be achieved.

The object of this invention is to provide a new composition for washing and conditioning hair, avoiding the disadvantages described above, and providing in a single operation the washing action of the shampoo and the reconditioning action of the conditioner.

The composition for washing and conditioning hair acting as a shampoo and as a conditioner according to this invention is distinguished in that it consists of an aqueous solution with a pH of between about 5 and 7, comprising:

(a.) about 8 to 20% by weight of at least one anionic surfactant;
(b.) about 1 to 3.5% by weight of at least one amine oxide having a conditioning effect;
(c.) about 0.2 to 3% of at least one cationic quaternary polymer having a conditioning effect;
the rest of the composition including known additives.

Of course, the composition according to the invention can further contain ingredients chosen from those commonly used in shampoos and conditioners such as foaming agents, thickeners, silicones, proteins, appropriate organic solvents, perfumes, dyes, preservatives, etc. All these conventional additives are chosed by the man skilled in the art in accordance with their compatibility and the results required.

It is also preferable to incorporate moisturizing agent and/or a sequestering agent in the composition to promote its hair applicability properties.

In addition, the incorporation of at least one amphoteric surfactant in a quantity representing at the most 6% by weight of the total weight of the composition, and preferably between 0.7 and 2% by weight can prove advantageous, according to this invention.

According to an advantageous form of embodiment of the invention, the moisturizing agent is an urea, or a derivative, present at the rate of about 1 to 5% by weight, and preferably 2 to 4% by weight with respect to the total weight of the composition. Such a compound used in such a quantity promotes the wetting action of the composition. Although its properties are well-known, urea is little used in products for the hair and its utilization in a composition combining a shampoo and a conditioner had not been considered yet.

The sequestering agent that may be used in the composition of this invention can be chosen from ethylene diamine tetracetic acid, nitrilotriacetic acid or polyphosphate. According to the invention, use is preferentially made of nitrilotriacetic acid at a rate of about 0.2 to 2% by weight of the total weight of the composition. Such a compound enables the lathering, application and rinsing properties of the composition according to the invention to be improved. According to a preferred embodiment, it is used at a rate of about 0.25 to 1% by weight.

As indicated above, the pH of the composition according to the invention is between about 5 and 7, that is, within a low acidity range, and preferentially between 5.5 and 6.5. The value of the pH depends of course on the various components used but, if necessary, it must be adjusted in the usual way, so that it falls within the aforementioned range. It is important to note that the classic amine oxides of technology are strongly substantive only at more acid pH values, that is, between about 3 and 4, and that an increase in the pH results in a reduction of their cationicity and substantivity. In correlation, the composition according to the invention provides at a slightly acid pH, an excellent conditioning action of the conditioner without an excessive substantive effect, in addition to a shampooing action, and it can be used with the same frequency as a classic shampoo.

The anionic and amphoteric surfactants used in this invention can be chosen from the compounds commonly used in shampoos and constitute a satisfactory washing base.

More particularly, the anionic surfactant, which is an essential component of the invention, is used at the rate of about 8 to 20% by weight of the total weight of the composition, and preferentially between 9 and 12% by weight. It is possible to use one or several surfactants in combination, an alkyl sulfate or an alkyl ether sulfate being used preferentially, whose properties are well-known in the field of shampoos.

Use can be made for example of an alkyl sulfate of general formula $ROSO_3M$, or an alkyl ether sulfate of general formula $R(OCH_2CH_2)_nOSO_3M$ in which R represents an alkyl group with 12 to 18 carbon atoms, M a metal cation, an $-NH_4$ group or an amino residue, and n is equal to 2 or 3; M is preferentially an alkali metal cation, such as sodium and potassium. The particularly preferred anionic surfactants entering into the above formula are sodium lauryl sulfate and sodium lauryl ether sulfate; other salts, such as potassium, ammonium and ethanolamines salts can also be used. Other known anionic surfactants, such as alkyl sulfonates or alkyl sulfosuccinates including preferentially 12 to 18 carbon atoms in the alkyl part, or else N-acyl sarcosinates of formula $RCONCH_3COOM$ where R is an alkyl group with 8 to 18 carbon atoms and M is a hydrogen atom or a metal cation, can also be used.

The anionic surfactant of the above general formula can be used alone or in combination with another surfactant of the same general formula, or with another different anionic surfactant. If the latter case, this other anionic surfactant can be chosen freely from known anionic surfactants, and use can be made for example of an alkali metal polypeptidate such as potassium cocopolypeptidate, an alkyl benzene sulfonate and, for example, sodium dodecyl benzene sulfonate, an alkyl diethanolamine or triethanolamine sulfate, etc.

According to the invention it is particularly advantageous to use an alkyl sulfate or an alkyl ether sulfate, and more particularly sodium lauryl sulfate or sodium lauryl ether sulfate in combination with an alkali metal polypeptidate, in particular potassium cocopolypeptidate, in a ratio by weight of between 15:1 and 5:1, and preferably about 10:1.

The amphoteric surfactant which can be used in the invention constitues a secondary component present in a quantity smaller than that of the anionic surfactant which is the principal component of the washing base. It represents less than about 6% by weight of the composition of the invention, and preferentially 0.7 to 2% by weight. Of course, it is possible to use a mixture of several amphoteric surfactants, but their total concentration must not represent more than about 30% of that of the anionic surfactants used.

In general, it can be chosen from the N-alkyl-$\beta$-amino propionates of formula $RNHCH_2CH_2COOM$, or the N-alkyl-B-imino dipropionates of formula $RN(CH_2CH_2COOM)_2$ in which R is an alkyl group with 8 to 18 carbon atoms and M is a hydrogen atom or a metal cation; betaines such as alkyl betaines of formula $R(CH_3)_2N^+CH_2COO^-$, amido-betaines $RCON^+(CH_3)_2CH_2COO^-$, or sulfobetaines of formula $RCON^+(CH_3)_2(CH_2)_3SO_3^-$, in which R is an alkyl group with 8 to 18 carbon atoms; imidazolines of formula:

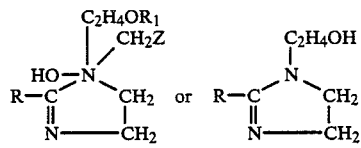

in which R is an alkyl group with 8 to 18 carbon atoms, $R_1$ is a hydrogen atom, a metal cation or a $-CH_2COOM$ group in which M is a hydrogen atom or a metal carbon, and Z is a $-COOM$ or $-CH_2COOM$ group where M is a hydrogen atom or a metal cation.

A preferred amphoteric surfactant according to this invention is cocoamido propyl betaine, preferably in combination with a hydrophilic phosphoamino lipid in a ratio by weight of about 9:1. For example, a combination of cocoamido propyl betaine and a lecithin modified to make it water-soluble can be used.

According to an advantageous form of embodiment of the invention the weight ratio of the anionic surfactant to the amphoteric surfactant is about 10:1.

The properties of the conditioner of the composition according to the invention are conferred by the combination of the amine oxide and the cationic quaternary polymer which, with the surfactants, constitute the essential components. This combination of components makes it possible to restore hair quality, in particular suppleness and sheen, and to improve its dressability, whether the hair be dry or damp.

According to the present invention, an amine oxide with a conditioning effect comprising at least one linear or branched alkyl group or alkylene chain containing at least 14 carbon atoms and preferably at least 16 carbon atoms, can be used.

The amine oxide is preferably represented by the general formula:

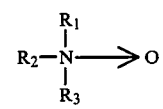

in which $R_1$ and $R_2$, identical or different, represent a lower alkyl group or a lower alkyl hydroxy group with 1 to 4 carbon atoms, and $R_3$ represents a linear or branched alkyl group with 14 to 20 carbon atoms, or a group of formula $R-CONH-R'-$in which R is a linear or branched alkyl group with 13 to 19 carbon atoms, and R' a divalent alkylene chain with 1 to 4 carbon atoms, the total number of carbon atoms then being at least equal to 15. The alkyl-group represented by $R_1$ and $R_2$ can be a methyl, ethyl, isopropyl or n-butyl group, but preferentially a methyl group. $R_3$, or R, if necessary, must be a ballast group including at least 13 carbon atoms, and R can be, for example, a linear alkyl group with 13 to 17 carbon atoms constituting, with the $-CO-$ group to which it is attached, respectively a myristyl or stearyl group.

These amine oxides are products known and available in commerce, generally prepared by reaction of a tertiary amine with hydrogen peroxide under controlled conditions. The starting tertiary amine can be, for example, an alkyl dimethyl amine, an alkylamidoalkyl dimethyl amine, an alkyl bis-hydroxypropyl amine, or else an alkyl morpholine.

According to this invention, preferential use is made of one or several amine oxides chosen from dimethyl stearyl amine, dimethyl cetyl amine oxide, dimethyl myristyl-cetyl amine oxide, and tallow-amido-propyl dimethyl amine oxide. These compounds confer not only conditioning properties, but also facilitate the emulsification and wettability.

The quantity of amine oxide used in the invention represents between 1 and 3.5% by weight of the composition, and preferentially between 1 and 3% by weight.

As indicated above, the amine oxide used in the invention are known products: for example, dimethyl stearyl amine oxide has already been incorporated in shampoo formulas for conditioning hair, or for reducing the irritation which surfactants can cause. They are also known as lathering agents, or lather stabilizers, according to the length of the alkyl chain of their molecule. On the other hand, they have not been used in combination with cationic quaternary polymers in defined proportions in specific matrix to formulate a composition which can act both as a shampoo and as an after-shampoo conditioner in a single application. The amine oxides used in this invention have the advantage of being compatible with the other components and not reacting with them, in particular with anionic surfactants. In addition, they act as slightly cationic compounds and reinforce the conditioning action of cationic quaternary polymers. By combining in determined proportions amine oxides and cationic quaternary polymers, which have a moderate substantivity as regards hair with an appropriate shampoo base in the composition of the invention according to the weight ratios indicated, it is possible to obtain excellent lathering properties and a conditioning effect without leaving an excessive deposit of conditioner on the hair.

The cationic quaternary polymer used in the invention enables the conditioning properties of the invention to be supplemented and improved while being compatible with the surfactants constituting the washing base. One or several cationic quaternary polymers can be used in the composition of the invention. It can be chosen from known quaternary polymers preferentially of light cationicity. Use can be made, for example, of certain quaternary ammonium salts derived from fatty acids, such as quaternium 27, copolymers of acrylamide and dimethyl diallyl ammonium chloride, such as polyquaternium 7, cellulose polymers derived from hydroxyethyl cellulose and triethyl ammonium epoxide such as polyquaternium 10, polymers derived from vinyl pyrrolidone, polymers resulting from the reaction of an alkyl sulfate with a copolymer of vinyl pyrrolidone and dialkylamino-ethyl methacrylate such as polyquaternium 11, or copolymers of acrylamide and methacryloyl alkyl ammonium chloride, etc.

The quantity of cationic quaternary polymer used in the invention is between about 0.2 and 3% by weight of the composition and preferentially between 0.2 and 1.5%.

Various additives habitually used in shampoos and conditioners can be incorporated in the composition of the invention in accordance with their properties and the results required. For example, one can add to the above components various dyes and perfumes, organic solvents such as alcohols or glycols, preservatives such as thiazolinone derivatives, and for example methyl-chlorothiazolinone, etc.

The composition according to this invention can be prepared by well-known conventional methods.

The following examples illustrate the invention without limiting its scope.

EXAMPLE 1

A composition according to this invention was prepared from the components indicated in table 1 below. In this table, all the percentages and parts are expressed as weights.

| Surfactants | |
| --- | --- |
| Sodium lauryl sulfate | 9.1% |
| Potassium cocopolypeptidate | 1.0% |
| Cocoamido propyl betaine | 0.9% |
| Modified lecithin | 0.1% |
| Amine oxides | |
| Dimethyl stearyl amine oxide | 1.3% |
| Dimethyl myristyl-cetyl amine oxide | 0.4% |
| Cationic quaternary polymers | |
| Polyquaternium 7 | 0.5% |
| Polyquaternium 10 | 0.2% |
| Moisturizing agent | |
| Urea | 3.0% |
| Sequestering agent | |
| Nitrilotriacetic acid | 1.0% |
| Miscellaneous | |
| Coco diethanolamide | 1.0% |
| Coco monoethanolamide | 0.8% |
| MEA undecylenamide | 0.1% |
| Ethylene glycol stearate | 1.2% |
| Amino methyl propanol | 0.6% |
| Panthenol ethyl-ether | 0.3% |
| Preservative (Kathon CG) | 0.1% |
| Butyl glycol | 1.0% |
| Infected ethyl alcohol | 1.0% |
| Dye, perfume | |
| Deionized | qs 100.0% |

The trials performed with the above composition, applied once to the hair, with addition of water and lathering, followed by rinsing gave excellent results.

Manageability was clearly improved compared with the usual shampoo and was equivalent to that provided by the successive uses of a shampoo and a classic conditioner. Sensorial assessments made in a hair laboratory, as well as an objective measurement of the combing forces by a dynamometric method showed a statistically significant improvement in distangling of dry hair and wet hair.

EXAMPLE 2

The same procedure as in Example 1 was followed using the components indicated below:

| Surfactants | |
| --- | --- |
| Sodium lauryl ether sulfate | 11.0% |
| Potassium cocopolypeptidate | 1.2% |
| Amine oxides | |
| Cetyl-myristyl dimethyl amine oxide | 0.5% |
| Tallow-amido-propyl dimethyl amine oxide | 0.5% |
| Dimethyl stearyl amine oxide | 0.5% |
| Cationic quaternary polymers | |
| Polyquaternium 11 | 0.6% |
| Polyquaternium 10 | 0.1% |
| Wetting agent | |
| Urea | 2.8% |
| Sequestering agent | |
| Ethylene diamine tetracetic acid | 0.9% |
| Miscellaneous | |
| Lauryl monoethanolamide | 1.0% |
| Lauryl diethanolamide | 0.6% |
| Ethylene glycol stearate | 1.0% |
| Amino methyl propanol | 0.5% |
| Panthenol ethyl-ether | 0.2% |
| Preservative (Kathon CG) | 0.1% |
| Butyl glycol | 1.0% |
| Infected ethyl alcohol | 1.0% |
| Dye, perfume | |
| Deionized water | qs 100.0% |

What is claimed is:

1. Composition for washing and conditioning hair providing the action of shampooing and conditioning, characterized in that it comprises an aqueous solution having a pH of about 5.5 to 6.5 consisting essentially of:
   (a.) from about 9 to 12% by weight of at least one anionic surfactant;
   (b.) from about 1 to 3% by weight of at least one amine oxide with a conditioning effect comprising at least one linear or branched alkyl group or alkylene chain containing at least 14 carbon atoms;
   (c.) from about 0.2 to 1.5% by weight of at least one cationic quaternary polymer with a conditioning action;
   (d.) from about 0.7 to 2% by weight of at least one amphoteric surfactant characterized in that the amphoteric surfactant is cocoamido propyl betaine in combination with a hydrophilic phosphoamino lipid, in a weight ratio of about 9:1; the remaining part of the composition comprising known additives.

* * * * *